(12) United States Patent
Peled

(10) Patent No.: US 11,834,677 B2
(45) Date of Patent: Dec. 5, 2023

(54) EXPANSION AND USE OF EXPANDED NK CELL FRACTIONS

(71) Applicant: Gamida Cell Ltd., Jerusalem (IL)

(72) Inventor: Tony Peled, Mevaseret Zion (IL)

(73) Assignee: Gamida Cell Ltd.

( * ) Notice: Subject to any disclaimer, the term of this patent is extended or adjusted under 35 U.S.C. 154(b) by 153 days.

(21) Appl. No.: 16/648,837

(22) PCT Filed: Sep. 27, 2018

(86) PCT No.: PCT/IB2018/057475
§ 371 (c)(1),
(2) Date: Mar. 19, 2020

(87) PCT Pub. No.: WO2019/069184
PCT Pub. Date: Apr. 11, 2019

(65) Prior Publication Data
US 2020/0263134 A1 Aug. 20, 2020

Related U.S. Application Data

(60) Provisional application No. 62/566,554, filed on Oct. 2, 2017.

(51) Int. Cl.
| | |
|---|---|
| *A61K 39/00* | (2006.01) |
| *C12N 5/0783* | (2010.01) |
| *A61K 35/17* | (2015.01) |
| *A61K 38/20* | (2006.01) |
| *A61K 39/395* | (2006.01) |
| *A61K 45/06* | (2006.01) |

(52) U.S. Cl.
CPC ............ *C12N 5/0646* (2013.01); *A61K 35/17* (2013.01); *A61K 38/2013* (2013.01); *A61K 39/39558* (2013.01); *A61K 45/06* (2013.01); *C12N 2500/38* (2013.01); *C12N 2501/2315* (2013.01)

(58) Field of Classification Search
None
See application file for complete search history.

(56) References Cited

U.S. PATENT DOCUMENTS

| | | | |
|---|---|---|---|
| 2007/0048290 A1 | 3/2007 | Tsai | |
| 2009/0011498 A1 | 1/2009 | Campana et al. | |
| 2013/0011376 A1* | 1/2013 | Peled | A61K 38/2013 435/375 |
| 2013/0131573 A1* | 5/2013 | Hildebrand | A61M 1/3486 530/403 |
| 2015/0152387 A1 | 6/2015 | Lee et al. | |
| 2015/0224143 A1 | 8/2015 | Malmberg et al. | |
| 2015/0225697 A1 | 8/2015 | Law et al. | |
| 2017/0002322 A1 | 1/2017 | Hariri et al. | |
| 2018/0021378 A1 | 1/2018 | Kang et al. | |

FOREIGN PATENT DOCUMENTS

| | | |
|---|---|---|
| CN | 102781449 A | 11/2012 |
| EP | 3252152 A1 | 12/2017 |
| WO | WO 2011/053322 A1 | 5/2011 |
| WO | WO 2011/080740 A1 | 7/2011 |
| WO | WO-2015195555 A1 | 12/2015 |
| WO | WO 2016/191756 A1 | 12/2016 |
| WO | WO 2017/037083 | * 3/2017 |
| WO | WO 2017/037083 A1 | 3/2017 |
| WO | WO 2017/077096 A1 | 5/2017 |
| WO | WO 2019/069184 A2 | 4/2019 |

OTHER PUBLICATIONS

Priesner (Human Gene Therapy, 2016, 27:860-869)(IDS).*
Keever-Taylor (ISCT Workshop #7, Medical College of Wisconsin, Poster Presentation, 40 pages, 2012)(IDS).*
Brecher et al (Clinical Microbiology Reviews, 2005, 18:195-204).*
Horwitz et al (The Journal of Clinical Investigation, 2014, 124:3121-3128).*
Spanholtz et al (PLOS, 2011, 6:e20740, internet pp. 1-11).*
Passweg et al (Leukemia, 2004, 18:1835-1838).*
Domogala et al (Cytotherapy, 2016, 18:754-759).*
Sutlu et al (Cytotherapy, 20-10, 12:1044-1055).*
Childs et al. "Bringing Natural Killer Cells to the Clinic: Ex Vivo Manipulation", Hematology, American Society of Hematology, Education Program, p. 234-246, 2012.
Frei et al. "Nicotinamide, A Form of Vitamin $B_3$, Promotes Expansion of Natural Killer Cells That Display Increased In Vivo Survival and Cytotoxic Activity", Blood, 118(21): # 4035, (2 pages), 2011.
Frias et al. "Generation of Functional Natural Killer and Dendritic Cells in A Human Stromal-Based Serum-Free Culture System Designed for Cord Blood Expansion", Experimental Hematology, 36(1): 61-68, 2008.
Gluck et al. "Phase I Studies of Interleukin (IL)-2 and Rituximab in B-Cell Non-Hodgkin's Lymphoma: IL-2 Mediated Natural Killer Cell Expansion Correlations With Clinical Response", Clinical Cancer Research, 10(7): 2253-2264, 2004.
Granzin et al. "Shaping of Natural Killer Cell Antitumor Activity by Ex Vivo Cultivation", Frontiers in Immunology, 8(Art.458): 1-18, Published Online 2017.
Greiner et al. "Culture Bag Systems for Clinical Applications of Adult Human Neural Crest-Derived Stem Cells", Stem Cell Research & Therapy, 5(2), (12 pages), Published Online 2014.

(Continued)

*Primary Examiner* — Laura B Goddard

(74) *Attorney, Agent, or Firm* — COOLEY LLP; Ivor R. Elrifi; Matthew Pavao

(57) ABSTRACT

Methods of expanding a natural killer (NK) cell fraction for transplantation into a subject are provided, and particularly, methods for providing transplantable NK cell fractions and protocols for their use, which can be employed for applications in cell transplants and infusions for treatment of cancer and other disease.

7 Claims, No Drawings

(56) References Cited

OTHER PUBLICATIONS

Harada et al. "A Wilms Tumor Cell Line, HFWT, Can Greatly Stimulate Proliferation of CD56+Human Natural Killer Cells and Their Novel Precursors in Blood Mononuclear Cells", Experimental Hematology, 32(7): 614-621, 2004.
Keever-Taylor "Perspectives in Cell Selection, Immunomagnetic Selection", ISCT Workshop #7, Medical College of Wisconsin, Poster Presentation, 40 pages, 2012.
Laport et al. "Adoptive Immunotherapy With Cytokine-Induced Killer Cells for Patients With Relapsed Hematologic Malignancies After Allogeneic Hematopoietic Cell Transplantation", Biology of Blood and Marrow Transplantation, 17(11): 1679-1687, 2011.
Peled et al. "Enhanced In Vivo Persistence and Proliferation of NK Cells Expanded in Culture With Small Molecule Nicotinamide: Development of A Clinical-Applicable Method for NK Expansion", 2017 59th ASH Annual Meeting, Atlanta, Georgia, USA, Dec. 9-12, 2017, Poster Presentation, (21 pages), 2017.
Priesner et al. "Automated Enrichment, Transduction, and Expansion of Clinical-Scale CD62L+T Cells for Manufacturing of Gene Therapy Medicinal Products", Human Gene Therapy, 27(10): 860-869, Published Online 2016.
Garg T. K. et al. "Highly activated and expanded natural killer cells for multiple myeloma immunotherapy", Haematologica, vol. 97. No. 9, 2012, pp. 1348-1356.
Lapteva N. et al. "Large-scale ex vivo expansion and characterization of natural killer cells for clinical applications", Cytotherapy, vol. 14, No. 9, 2012, pp. 1131-1143.
Shi J. et al. "Infusion of haplo-identical killer immunoglobulin-like receptor ligand mismatched NK cells for relapsed myeloma in the setting of autologous stem cell transplantation", British Journal of Haematology, vol. 143, No. 5, 2008, pp. 641-653.
Frei et al. "Improved Homing to Bone Marrow, Spleen and Lung of Adoptively Infused NK Cells Expanded Ex Vivo With The Small Molecule Nicotinamide Using Feeder-Free Conditions", Blood, 2013, vol. 122, No. 21, p. 897.
NCT03019666, ClinicalTrial "Ph I Trial of NAM NK Cells and IL-2 for Adult Pts with MM and NHL", ClinicalTrials.gov. ClincalTrials.gov. p .1-9. Jan. 12, 2017.

\* cited by examiner

EXPANSION AND USE OF EXPANDED NK CELL FRACTIONS

CROSS-REFERENCE TO RELATED APPLICATIONS

This application is a U.S. National Phase Application, filed under 35 USC § 371, of International Application No. PCT/IB2018/057475, filed on Sep. 27, 2018, which claims the benefit of priority under 35 USC § 119(e) of U.S. Provisional Patent Application No. 62/566,554 filed on Oct. 2, 2017. The contents of each of these applications is herein incorporated by reference in their entirety.

FIELD AND BACKGROUND OF THE INVENTION

The present invention relates to methods of expanding natural killer (NK) cells, selection of expanded NK cell populations for transplantation to subjects in need thereof and the therapeutic use of suitable, ex-vivo expanded NK cell fractions for transplantation in the clinical setting, for treatment of hematological malignancies. The present invention also envisions kits comprising the expanded NK cell fractions.

Natural killer (hereinafter also abbreviated as "NK") cells are lymphoid cells that participate in immune reactions. These cells have a variety of functions, especially the killing of tumor cells, cells undergoing oncogenic transformation and other abnormal cells in a living body, and are important components of innate immunological surveillance mechanisms. Clinical experience with adoptive immunotherapy with NK cells has emphasized the need for better methods for effectively and efficiently expanding NK cell populations while maintaining, and even enhancing their functionality in-vivo (killing ability, trafficking, localization, persistence and proliferation).

Unlike T cells, natural killer (NK) cells do not require the presence of a specific tumor antigen to kill cancer cells; rather their recognition of targets is regulated through the balance between activating and inhibitory signals. This ability of natural killer (NK) cells to kill tumor cells without the need to recognize a tumor-specific antigen provides advantages over T cells and makes them appealing for investigation as effectors for immunotherapy. NK cells have drawn considerable attention in recent years as a promising tool for immunotherapy in patients with various refractory hematological malignancies and metastatic solid tumors. However, despite NK cells' ability to kill cancer cells independently of antigen recognition, the full therapeutic potential of NK cell-based immunotherapy has yet to be realized. Results to date from experimental protocols have been limited mostly to partial responses, with marginal efficacy being attributed mainly to the relatively low number of NK cells infused, their short in vivo persistence, and/or their poor functionality in vivo. Therefore, development of ex vivo NK culture methods that both effectively expand the NK population and increase the functionality of adoptively infused NK cells in vivo is fundamental to improving the clinical applicability of NK cell immunotherapy.

Several methods for in-vitro expansion and activation of NK cells have been investigated. These include culturing NK cells enriched from PBMC overnight and long-term with cytokines, or co-culturing NK cells with feeder cells such as PBMC, genetically modified K562 cells (see US 20150224143 to Malmberg et al.), and Epstein-Barr virus-transformed lymphoblastoid cell lines (see, for example, US 20150152387 to Lee, et al). Other methods for the propagation of NK cells have been described: Frias et al. (Exp Hematol 2008; 36: 61-68) grew NK progenitors (CD7$^+$CD34$^-$Lin$^-$CD56$^-$) selected from cord blood on stromal cell layers with a serum-free medium, inducing NK differentiation with SCF, IL-7, IL-15, FL and IL-2, producing increased numbers of cytotoxic cultured NK cells. Harada et al. (Exp Hematol. 2004; 32:614-21) grew NK cells on cells from a Wilm's tumor cells line. Waldmann et al. (US20070160578) describes enhanced proliferation of NK and CD8-T cells from whole blood, bone marrow or spleen cells in culture using complexes of IL-15/R-ligand activator, in order to reduce undesirable cytokine production. Campana et al. (US20090011498) describes ex-vivo culture and activation of NK cells, for transplantation, in the presence of leukemia cells expressing IL-15 and 4-1BB, and having weak or absent MHC-I or II expression. Childs et al. (US20090104170) describes ex-vivo proliferation, and activation of NK cells by co-culture with irradiated EBV-transformed lymphoblastoid cells, in the presence of IL-2. Using another approach, Tsai (US20070048290) produced continuous NK cell lines from hematopoietic stem cells by ex-vivo culture of immortalized NK-progenitors with irradiated 3T3-derived OP-9S cells, for research and potential therapeutic applications (All the above-mentioned references are incorporated herein by reference).

Therapeutic use of expanded populations of NK cells has been the subject of more than 40 completed, active, recruiting or authorized clinical trials (see clinical trials (dot)gov website) investigating application of NK cells expanded by different protocols for the treatment of a variety of cancerous conditions, including hematological malignancies and solid tumors. Expanded NK cell populations have been found, in general, to maintain cytotoxicity. However, results to date underscore the difficulty in designing NK expansion and therapy protocols that are not only safe but sufficiently effective in targeting different forms of malignancies.

The present inventors have described efficient ex-vivo expansion and enhanced functionality of NK cells cultured with cytokines and the NAD precursor nicotinamide, reporting increased localization and engraftment of the expanded NK cells into target organs (e.g., spleen, bone marrow and peripheral blood) in animal models (see PCT Publication WO2011/080740 and Frei, et al, Blood, 2011; 118:4035).

SUMMARY OF THE INVENTION

According to an aspect of some embodiments of the present invention there is provided a method of preparing a transplantable NK cell fraction for transplantation into a subject in need thereof, the method comprising:
(a) obtaining a CD3-depleted NK cell fraction HLA-haploidentical or HLA-mismatched for the subject;
(b) ex vivo culturing the CD3-depleted NK cell fraction under conditions allowing for cell proliferation, wherein the conditions comprise providing nutrients, serum, IL-15 and nicotinamide in an amount between 1.0 mM to 10 mM;
(c) supplementing the CD3-depleted NK cell fraction with fresh nutrients, serum, IL-15 and nicotinamide 8-10 days following step (b) to produce an expanded CD3-depleted NK cell fraction;
(d) harvesting the expanded CD3-depleted NK cell fraction 14-16 days following step (b); and
(e) washing and concentrating the expanded CD3-depleted NK cell fraction of step (d), thereby producing a transplantable NK cell fraction for transplantation in the subject.

According to some embodiments of the present invention the CD3-depleted NK cell fraction is a human NK cell fraction.

According to some embodiments of the present invention the CD3-depleted NK cell fraction is from apheresis.

According to some embodiments of the present invention the ex-vivo culturing is devoid of a feeder layer.

According to some embodiments of the present invention the serum is human serum.

According to some embodiments of the present invention the conditions for allowing for cell proliferation comprise providing 10% human serum.

According to some embodiments of the present invention the IL-15 comprises 20 ng/ml IL-15.

According to some embodiments of the present invention the nicotinamide comprises 5.0 mM nicotinamide.

According to some embodiments of the present invention the method comprises providing nutrients comprising minimal essential cell culture medium.

According to some embodiments of the present invention the NK cell fraction is from an HLA-haploidentical or HLA-mismatched donor having at least:
  (a) HLA matching at intermediate resolution DNA-based Class 1 typing of the A and B locus of at least 2/4 class 1 allele; and
  (b) absence of (MFI≤1000) recipient donor-specific anti-HLA antibodies.

According to some embodiments of the present invention the NK cells of step (a) comprise at least 40-90% CD56+/CD3− cells.

According to some embodiments of the present invention the harvesting of step (d) comprises harvesting a first portion of the expanded CD3-depleted NK cell fraction 14 days following step (b), and harvesting a second portion of the expanded CD3-depleted NK cell fraction 16 days following step (b).

According to some embodiments of the present invention the first portion comprises about 50% of the expanded CD3-depleted NK cell fraction and the second portion comprises the remainder of the expanded CD3-depleted NK cell fraction.

According to some embodiments of the present invention the washed and concentrated expanded NK cell fraction of generated by step (e) is characterized by the following parameters:
  (a) at least 70% CD56+/CD3− cells;
  (b) at least 70% viability;
  (c) fewer than $5.0 \times 10^5$ CD3+ cells/Kg mass of patient, upon infusion;
  (d) no more than 5 EU endotoxin/Kg mass of patient, upon infusion, and
  (e) no Gram-positive micro-organisms.

According to some embodiments of the present invention the culturing of step (b) is affected in flasks at $200\text{-}300 \times 10^6$ cells per flask.

According to an aspect of some embodiments of the present invention there is provided a transplantable NK cell fraction prepared according to the methods of the invention.

According to some embodiments of the present invention the transplantable NK cell fraction is characterized by the following parameters:
  (a) at least 70% CD56+/CD3− cells;
  (b) at least 70% viability;
  (c) fewer than $5.0 \times 10^5$ CD3+ cells/Kg mass of patient, upon infusion;
  (d) no more than 5 EU endotoxin/Kg mass of patient, upon infusion, and
  (e) no Gram-positive micro-organisms.

According to some embodiments of the present invention the transplantable NK cell fraction is provided in a fluorinated ethylene propylene (FEP) culture bag.

According to an aspect of some embodiments of the present invention there is provided a transplantable human NK cell fraction characterized by the following parameters:
  (a) at least 70% CD56+/CD3− cells;
  (b) at least 70% viability;
  (c) fewer than $5.0 \times 10^5$ CD3+ cells/Kg mass of patient, upon infusion;
  (d) no more than 5 EU endotoxin/Kg mass of patient, upon infusion, and
  (e) no Gram-positive micro-organisms.

According to an aspect of some embodiments of the present invention there is provided a method of treating a hematological disease in a subject in need thereof, the method comprising:
  (a) administering an anti-cancer monoclonal antibody to the subject;
  (b) administering at least one immunosuppressive agent to the subject;
  (c) transplanting an expanded CD3-depleted haploidentical or mismatched NK cell fraction into the subject in need thereof, wherein the expanded CD3-depleted HLA-haploidentical or HLA-mismatched NK cell fraction has been expanded by ex-vivo culturing with nutrients, serum, IL-15 and nicotinamide in an amount between 1.0 mM to 10 mM; and
  (d) administering IL-2 to the subject,
thereby treating the hematological disease in the subject.

According to some embodiments of the present invention the subject and the NK cell fraction are a human subject and a human NK cell fraction.

According to some embodiments of the present invention the immunosuppressive agent is a chemotherapeutic immunosuppressive agent and/or irradiation.

According to some embodiments of the present invention the hematological disease is a hematological malignancy.

According to some embodiments of the present invention the hematological disease is multiple myeloma.

According to some embodiments of the present invention the multiple myeloma is characterized by at least one of:
  (a) relapsed disease between 2-18 months following first autologous stem cell transplantation;
  (b) relapsed disease at least 4 months following allogeneic stem cell transplantation with no evidence of active graft versus host disease (GVHD);
  (c) relapsed/refractory disease following at least two lines of therapy including proteasome inhibitor and an immunomodulatory drug (IMiD);
  (d) Serum IgG, IgA, IgM or IgD Myeloma protein (M-protein) greater than or equal to 0.5 g/dL; and
  (e) Urine M-protein greater than or equal to 200 mg/24 collection.

According to some embodiments of the present invention the hematological disease is non-Hodgkins lymphoma (NHL).

According to some embodiments of the present invention the NHL is CD20 positive B cell NHL.

According to some embodiments of the present invention the NHL is characterized by at least one of:
(a) relapsed/refractory disease that has failed conventional therapy;
(b) relapsed disease at least 60 days following autologous stem cell transplantation;
(c) relapsed disease at least 4 months following allogeneic stem cell transplantation with no evidence of active graft versus host disease; and
(d) measurable disease greater than or equal to 1.5 cm in diameter.

According to some embodiments of the present invention the hematological malignancy is multiple myeloma and the anticancer monoclonal antibody is Elotuzumab (10 mg/kg).

According to some embodiments of the present invention the hematological malignancy is NHL and the anticancer monoclonal antibody is Rituximab (375 mg/m$^2$).

According to some embodiments of the present invention step (a) is performed three times.

According to some embodiments of the present invention step (d) comprises administering a first dose of the expanded CD3-depleted haploidentical or mismatched NK cell fraction followed two days later by a second dose of the expanded CD3-depleted haploidentical or mismatched NK cell fraction.

According to some embodiments of the present invention step (a) is performed three times: at 9-11 days before the first dose, at 3 days before the first dose and at 11 days following the first dose of the expanded CD3-depleted haploidentical or mismatched NK cell fraction.

According to some embodiments of the present invention step NK cell fraction comprises between $1\times10^7$/kg and $5\times10^8$/kg expanded CD3-depleted HLA-haploidentical or HLA-mismatched NK cells.

According to some embodiments of the present invention the combined first and the second doses comprise $2\times10^7$/kg to $2\times10^8$/kg total expanded CD3-depleted HLA-haploidentical or HLA-mismatched NK cells.

According to some embodiments of the present invention:
(a) the first dose and the second dose of the NK cell fraction each comprise $1\times10^7$/kg expanded CD3-depleted haploidentical or mismatched NK cells, for a total dose of $2\times10^7$/kg expanded CD3-depleted haploidentical or mismatched NK cells, or
(b) the first dose and the second dose of the NK cell fraction each comprise $5\times10^7$/kg expanded CD3-depleted haploidentical or mismatched NK cells, for a total dose of $1\times10^8$/kg expanded CD3-depleted haploidentical or mismatched NK cells, or
(c) the first dose and the second dose of the NK cell fraction each comprise $1\times10^8$/kg expanded CD3-depleted haploidentical or mismatched NK cells, for a total dose of $2\times10^8$/kg expanded CD3-depleted haploidentical or mismatched NK cells.

According to some embodiments of the present invention the expanded CD3-depleted HLA-haploidentical or HLA-mismatched NK cell fraction is administered to the subject no more than 1 hour later after provision of the fraction for transplantation and no more than 10 hours following final product release of the fraction.

According to some embodiments of the present invention the expanded CD3-depleted haploidentical or mismatched NK cell fraction is administered to the subject by infusion without a filter or pump, for a duration of no less than 15 and no more than 60 minutes.

According to some embodiments of the present invention the at least one immunosuppressive agent comprises cyclophosphamide and/or fludarabine.

According to some embodiments of the present invention:
(i) the at least one immunosuppressive agent comprises both cyclophosphamide (40 mg/kg) and fludarabine (25 mg/m$^2$); and
(ii) the cyclophosphamide is administered 5 days prior to transfusion of the expanded CD3-depleted haploidentical or mismatched NK cells, and the fludarabine is administered on each one of days 5, 4 and 3 prior to transfusion of the expanded CD3-depleted HLA-haploidentical or HLA-mismatched NK cells.

According to some embodiments the method of the present invention further comprises administering $6\times10^6$ units IL-2 following transfusion of the expanded CD3-depleted NK cells:
(i) on the day of transfusion of the expanded CD3-depleted HLA-haploidentical or mismatched NK cells; and
(ii) two days following transfusion of the expanded CD3-depleted haploidentical or mismatched NK cells; and
(iii) four days transfusion of the expanded CD3-depleted haploidentical or mismatched NK cells.

According to some embodiments of the present invention the method comprises transplanting a transplantable NK cell fraction prepared according to any of the methods of preparing a transplantable expanded NK cell fraction as detailed herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DETAILED DESCRIPTION OF EMBODIMENTS OF THE INVENTION

The present invention is of methods of expanding a natural killer (NK) cell fraction for transplantation into a subject, while at the same time, maintaining or enhancing function of the cells ex-vivo and/or in-vivo. In one embodiment, ex-vivo culture of NK cells with a nicotinamide and/or other nicotinamide moiety and NK cell growth factors facilitates the production of NK cell populations for use as a therapeutic ex-vivo expanded NK cell preparation, which includes an expanded population of functional NK cells having parameters suitable for infusion into a subject (e.g. robust expansion of NK cells alongside a reduced CD3+ T cell fraction). Specifically in this respect, the present invention can be used to provide transplantable NK cell fractions and protocols for their use, which can be employed for applications in cell transplants and infusions for treatment of cancer and other disease. Non-limiting applications may include allogeneic adoptive immunotherapy and combination immunotherapy along with sensitizing agents and other anti-cancer modalities.

The principles and operation of the present invention may be better understood with reference to the accompanying descriptions.

Before explaining at least one embodiment of the invention in detail, it is to be understood that the invention is not necessarily limited in its application to the details set forth in the following description. The invention is capable of other embodiments or of being practiced or carried out in various ways.

Natural killer (hereinafter also abbreviated as "NK") cells are lymphoid cells that participate in immune reactions, exhibiting spontaneous non-MHC-restricted cytotoxic activity against tumor cells. Thus, developing clinical-grade protocols (e.g., no stromal layer, minimal cytokines) for effectively ex-vivo expanding the number of viable NK cells and effectively enhancing their function, as well as likelihood of homing to lymph nodes and their homeostatic proliferation in-vivo following infusion, could improve the success of adoptive immunotherapy with NK cells for the treatment of cancerous conditions, such as solid tumors, hematopoietic malignancies and the like.

The present invention provides clinically appropriate conditions for preparing and characterizing expanded NK cell fractions suitable for transplantation, in the clinical setting, based on culturing NK cells with nicotinamide, above a certain concentration, as is further detailed herein. As such, in embodiments thereof, the present invention provides clinically appropriate culture conditions for production of transplantable NK cell fraction of functionally mature NK cells, without accompanying induction of non-NK cell (e.g. CD3+) proliferation, transplantable NK fractions and criteria for their selection, as well as clinical protocols for their use in treatment of cancerous disease, in particular, hematological malignancies.

Thus, according to one aspect of an embodiment of the present invention there is provided a method of preparing a transplantable NK cell fraction for transplantation into a subject in need thereof, the method comprising:
(a) obtaining a CD3-depleted NK cell fraction HLA-haploidentical or HLA-mismatched for said subject;
(b) ex vivo culturing said CD3-depleted NK cell fraction under conditions allowing for cell proliferation, wherein said conditions comprise providing nutrients, serum, IL-15 and nicotinamide in an amount between 1.0 mM to 10 mM;
(c) supplementing said CD3-depleted NK cell fraction with fresh nutrients, serum, IL-15 and nicotinamide 8-10 days following step (b) to produce an expanded CD3-depleted NK cell fraction;
(d) harvesting said expanded CD3-depleted NK cell fraction 14-16 days following step (b); and
(e) washing and concentrating said expanded CD3-depleted NK cell fraction of step (d),
thereby producing a transplantable NK cell fraction for transplantation into said subject.

As used herein, the term natural killer (NK) cells refers to large granular lymphocytes involved in the innate immune response. Functionally, NK cells exhibit cytolytic activity against a variety of targets via exocytosis of cytoplasmic granules containing a variety of proteins, including perforin, and granzyme proteases. Killing is triggered in a contact-dependent, non-phagocytotic process which does not require prior sensitization to an antigen. Human NK cells are characterized by the presence of the cell-surface markers CD16 and CD56, and the absence of the T cell receptor (CD3). Human bone marrow-derived NK cells are further characterized by the CD2+CD16+CD56+CD3− phenotype, further containing the T-cell receptor zeta-chain [zeta($\zeta$)-TCR], and often characterized by NKp46, NKp30 or NKp44. Non-NK cells such as NKT cells or CD8NKT possess characteristics and cell-surface markers of both T cells and NK cells. In one embodiment, the method of the present invention is employed for ex-vivo propagation of mature NK cells from a population of cells. As used herein, the term "mature NK cell" is defined as a committed NK cell, having characteristic surface markers and NK cell function, and lacking the potential for further differentiation. As use herein, mature NK cells include, but are not limited to $CD56^{bright}$ cells, which can proliferate and produce abundant cytokines, $CD56^{dim}$ cells, exhibiting robust cytotoxicity, $CD56^{bright}CD94^{high}$ and $CD56^{dim}CD94^{high}$ cells. In another embodiment, NK progenitor cells, or mixed populations of NK progenitor cells and mature NK cells are propagated. Cell surface expression of the CD56, CD3, CD94 and other markers can be determined, for example, via FACS analysis or immunohistological staining techniques.

As used herein, the term "progenitor" refers to an immature cell capable of dividing and/or undergoing differentiation into one or more mature effector cells. Lymphocyte progenitors include, for example, pluripotent hematopoietic stem cells capable of giving rise to mature cells of the B cell, T cell and NK lineages. In the B cell lineage (that is, in the developmental pathway that gives rise to mature B cells), progenitor cells also include pro-B cells and pre-B cells characterized by immunoglobulin gene rearrangement and expression. In the T and NK cell lineages, progenitor cells also include bone-marrow derived bipotential T/NK cell progenitors [e.g., CD34(+)CD45RA(hi)CD7(+) and CD34(+)CD45RA(hi)Lin(−)CD10(+) cells], as well as intrathymic progenitor cells, including double negative (with respect to CD4 and CD8) and double positive thymocytes (T cell lineage) and committed NK cell progenitors.

NK cells of the present invention may be derived from any source which comprises such cells. NK cells are found in many tissues, and can be obtained, for example, from lymph nodes, spleen, liver, lungs, intestines, deciduas and can also be obtained from iPS cells or embryonic stem cells (ESC). Typically, cord blood, peripheral blood, mobilized peripheral blood and bone marrow, which contain heterogeneous lymphocyte cell populations, are used to provide large numbers of NK cells for research and clinical use.

Clinical experience with NK cell transplantation has shown that allogeneic NK cells can successfully engraft in hosts, with a lower incidence of graft versus host disease (GVHD). When the identity of the candidate for transplantation (e.g., the "subject") is known, parameters such as HLA-match (compatibility) can be determined and serve as a selection criteria.

Thus, according to specific embodiments, the NK cell fraction is from an HLA-haploidentical or HLA-mismatched donor. The NK cell donor can be related, or non-related donor.

In particular embodiments, NK cells selected for ex-vivo expansion are from donors HLA-matching of at least 2 out of 4 HLA class I (intermediate resolution DNA-based Class I typing of the HLA-A and HLA-B loci), of at least 3 out of 4 HLA class I (intermediate resolution DNA-based Class I typing of the HLA-A and HLA-B loci), or of 4 out of 4 HLA class I (intermediate resolution DNA-based Class I typing of the HLA-A and HLA-B loci) loci with the subject. According to certain embodiments, the apheresis units are from donors having at least 2 out of 4 HLA class I (intermediate resolution DNA-based Class I typing of the HLA-A and HLA-B loci) and absence of (Mean Fluorescence Intensity (MFI)≤1000) recipient (host, subject) donor-specific anti-HLA antibodies. MFI values represent the amount, or titer of the antibody(ies). Typically, Class I HLA (or Major Histocompatability Complex, MHC) antigens are determined on the NK cells by a microcytotoxicity assay using alloantisera for specific HLAs, complement for cytotoxicity and a dye to identify killed cells. HLA Class II are typically determined by the mixed lymphocyte reaction (MLR), measuring lymphocyte proliferation following culture of mixed lymphocyte populations. HLA DR antigens can be identified by B cell antisera in a microcytotoxicity assay with enriched B cells. Antisera can be replaced by specific monoclonal antibodies.

Another common method for collecting blood fractions is apheresis, in which whole donor blood is separated into blood components (e.g. plasma, leukocytes and erythrocytes), typically by centrifugation, selected components are drawn off for manipulation (e.g. culturing of leukocyte fractions) and the remainder is returned to the donor. Apheresis has the advantage of providing specific blood fractions (for example, leukocyte fraction) in large numbers without depleting fluids (e.g. plasma) and other blood components. Apheresis can be based on continuous flow centrifugation, which requires a low extracorporeal volume, or based on intermittent flow centrifugation of the blood, which separates the components in cycles, but is typically more time consuming and characterized by larger extracorporeal volumes of the donor's blood. Many suitable apheresis devices are commercially available. Typically, apheresis applies to separation of blood components from the peripheral blood of the donor.

Thus, according to one aspect of one embodiment of the present invention, the method comprises culturing a CD3-depleted NK cell fraction wherein the NK cell fraction is from apheresis. In specific embodiments, the NK cell fraction is from apheresis units obtained from donors using a PCS2 or MCS8150 Haemonetics apheresis machine (Haemonetics, Boston, MA). In certain embodiments, the NK cell fraction is from apheresis units obtained from peripheral blood of the donor.

In some embodiments NK cells can be cultured from fresh cell populations, while other embodiments culture NK cells from stored cell populations (such as cyropreserved and thawed cells) or previously cultured cell populations.

Lymphocyte fractions, such as "buffy coat" or apheresis units can be processed to enrich or purify or isolate specific defined populations of cells. The terms "purify" and "isolate" do not require absolute purity; rather, these are intended as relative terms. Thus, for example, a purified lymphocyte population is one in which the specified cells are more enriched than such cells are in its source tissue. A preparation of substantially pure lymphocytes can be enriched such that the desired cells represent at least 50% of the total cells present in the preparation. In certain embodiments, a substantially pure population of cells represents at least 60%, at least 70%, at least 80%, at least 85%, at least 90%, or at least 95% or more of the total cells in the preparation.

Methods for enriching and isolating lymphocytes are well known in the art, and appropriate methods can be selected based on the desired population. For example, in one approach, the source material is enriched for lymphocytes by removing red blood cells. Based on density red blood cells are separated from lymphocytes and other cells. The lymphocyte rich fractions can then be selectively recovered. Lymphocytes and their progenitors can also be enriched by centrifugation using separation mediums such as standard Lymphocyte Separation Medium (LSM) available from a variety of commercial sources. Alternatively, lymphocytes/ progenitors can be enriched using various affinity based procedures. Numerous antibody mediated affinity preparation methods are known in the art such as antibody conjugated magnetic beads. Lymphocyte enrichment can also be performed using commercially available preparations for negatively selecting unwanted cells, such as FICOLL-HYPAQUE™ and other density gradient mediums formulated for the enrichment of whole lymphocytes, T cells or NK cells.

Methods of selection of NK cells from blood, bone marrow, lymphocyte preparations (e.g. apheresis units) or tissue samples are well known in the art (see, for example, U.S. Pat. No. 5,770,387 to Litwin et al) (which is incorporated herein in its entirety by reference). Most commonly used are protocols based on isolation and purification of CD56+ cells, usually following mononuclear cell fractionation, and depletion of non-NK cells such as CD3+, CD34+, CD133+ and the like. Combinations of two or more protocols can be employed to provide NK cell populations having greater purity from non-NK contaminants. The purity of the NK cell preparation is of great significance for clinical applications, as non-NK cells, such as T-cells and NKT cells, contribute to antigen-specific reactions such as GVHD, compromising the potential benefits of NK cell transplantation. Commercially available kits for isolation of NK cells include one-step procedures (for example, CD56 microbeads and CD56+, CD56+CD16+ isolation kits from Miltenyi Biotec, Auburn CA), and multistep procedures, including depletion, or partial depletion, of CD3+ or depletion with non-NK cell antibodies recognizing and removing T cells (for example, OKT-3), B cells, stem cells, dendritic cells, monocytes, granulocytes and erythroid cells. Thus, in certain embodiments, the NK cell population is selected or enriched for NK cells, and can be a CD3-depleted NK cell fraction. In some embodiments, the CD3-depleted fraction comprises CD56+CD16+CD3− cells and or CD56+CD16−CD3−. In specific embodiments, the NK cells selected for culture comprise at least 40% CD56+/CD3− cells, at least 50% CD56+/CD3− cells, at least 60% CD56+/CD3− cells, at least 70% CD56+/CD3− cells, at least 80% CD56+/CD3− cells or at least 90% CD56+/CD3− cells. In some embodiments, the NK cells selected for culture comprise between 40%-90% CD56+/CD3− cells, between 50%-80% CD56+/CD3− cells, between 55-75% CD56+/CD3− cells, between 60%-70% CD56+/CD3− cells. In some embodiments, the NK cells selected for culture comprise between 40 and 90% CD56+/CD3− cells.

Methods for selection of NK cells according to phenotype include, but not exclusively, immunodetection and FACS analysis. In specific embodiments, the NK cell fraction is depleted of CD3 cells by immunomagnetic selection, for example, using a CliniMACS T cell depletion set ((LS Depletion set (162-01) Miltenyi Biotec).

In further embodiments, the CD3-depleted NK cell fraction is treated to remove any trace erythrocytes. Thus, in some embodiments, following CD3 cell depletion, the NK cell fraction undergoes red blood cell (RBC) lysis before culturing. In specific embodiments, red blood cell lysis is accomplished using ammonium chloride potassium (ACK) buffer (Gibco, Thermo Fischer Scientific).

NK cells can be cultured ex-vivo by short or long term culture. The present inventors have demonstrated that NK cells can be cultured with growth factors and nicotinamide and/or other nicotinamide moiety, for as little as 7 days, or as many as 3 weeks resulted in enhanced, preferential proliferation and/or functionality of the cultured NK cells, as compared to cells cultured with cytokines but with less than 0.1 mM nicotinamide and/or other nicotinamide moiety (see PCT Publication WO2011/080740). In preparing a clinically suitable NK cell fraction for transplantation, it is desirable to provide significant ex-vivo NK cell expansion while retaining therapeutically advantageous functionality of the expanded NK cell fractions, without requiring lengthy treatment duration.

Thus, in specific embodiments, the CD3-depleted NK cell fraction is cultured over a period of 14-16 days.

Ex-vivo culturing of NK cells can be effected, according to this aspect of the present invention, by providing NK cells ex vivo with conditions for cell proliferation and ex vivo culturing the NK cells with a nicotinamide moiety, thereby ex-vivo expanding the population of NK cells.

As used herein "culturing" includes providing the chemical and physical conditions (e.g., temperature, gas) which are required for NK cell maintenance, and growth factors. In one embodiment, culturing the NK cells includes providing the NK cells with conditions for NK cell proliferation. Examples of chemical conditions which may support NK cell proliferation include but are not limited to buffers, nutrients, serum, vitamins and antibiotics as well as cytokines and other growth factors which are typically provided in the growth (i.e., culture) medium. In a particular embodiment, conditions for cell proliferation comprise nutrients, serum and cytokine(s).

In one embodiment, the NK culture medium includes a minimal essential medium (MEM), such as MEMα (BI, Bet HaEmek, Israel) and serum. In some embodiments, the serum is provided at 2-20%, 5-15% or 5-10% of the culture medium. In specific embodiments, the serum is human serum, provided at 10% of the culture medium. In a particular embodiment, the culture medium is MEMα comprising 10% Human AB Serum (Sigma-Aldrich, St. Louis, MO). Other media suitable for use with the invention include, but are not limited to Glascow's medium (Gibco Carlsbad CA), RPMI medium (Sigma-Aldrich, St Louis MO) or DMEM (Sigma-Aldrich, St Louis MO). It will be noted that many of the culture media contain nicotinamide as a vitamin supplement for example, MEMα (8.19 µM nicotinamide), RPMI (8.19 µM nicotinamide), DMEM (32.78 µM nicotinamide) and Glascow's medium (16.39 µM nicotinamide), however, the methods of the present invention relate to exogenously added nicotinamide supplementing any nicotinamide and/or nicotinamide moiety included the medium's formula, or that resulting from overall adjustment of medium component concentrations.

According to some embodiments of the present invention, culturing the NK cells under conditions allowing for cell proliferation comprises providing the cells with nutrients, serum and cytokines. In some embodiments the at least one growth factor includes cytokines and/or chemokines. Cytokines and other growth factors are typically provided in concentrations ranging from 0.5-100 ng/ml, or 1.0-80 ng/ml, more typically 5-750 ng/ml, yet more typically 5.0-50 ng/ml (up to 10× such concentrations may be contemplated), and are available commercially, for example, from Perpo Tech, Inc., Rocky Hill, NJ, USA. In one embodiment, conditions allowing for cell proliferation includes providing the cytokine interleukin 15 (IL-15). In specific embodiments, the CD3-depleted NK cells are cultured with 20 ng/ml IL-15.

Further, it will be appreciated in this respect that novel cytokines are continuously discovered, some of which may find uses in the methods of NK cell proliferation of the present invention. For applications, in which cells are introduced (or reintroduced) into a human subject, it is often preferable to use serum-free formulations, such as AIM V® serum free medium for lymphocyte culture or MARROW-MAX® bone marrow medium. Such medium formulations and supplements are available from commercial sources such as Invitrogen (GIBCO) (Carlsbad, Calif.). The cultures can be supplemented with amino acids, antibiotics, and/or with cytokines to promote optimal viability, proliferation, functionality and/or and survival.

According to one embodiment, the NK cell fraction is cultured with nutrients, serum, a cytokine (e.g. IL-15) and nicotinamide and/or a nicotinamide moiety. As used herein, the term "nicotinamide moiety" refers to nicotinamide as well as to products that are derived from nicotinamide, derivatives, analogs and metabolites thereof, such as, for example, NAD, NADH and NADPH, which are capable of effectively and preferentially enhancing NK cell proliferation and/or activation. Nicotinamide derivatives, analogs and metabolites can be screened and evaluated for their effect on ex-vivo NK proliferation in culture by addition to NK cultures maintained as described hereinbelow, addition to functional assays such as killing and motility assays, or in automated screening protocols designed for high-throughput assays well known in the art.

As used herein, the phrase "nicotinamide analog" refers to any molecule that is known to act similarly to nicotinamide in the abovementioned or similar assays. Representative examples of nicotinamide analogs can include, without limitation, benzamide, nicotinethioamide (the thiol analog of nicotinamide), nicotinic acid and α-amino-3-indolepropionic acid.

The phrase "nicotinamide derivative" further refers to any structural derivative of nicotinamide itself or of an analog of nicotinamide. Examples of such derivatives include, without limitation, substituted benzamides, substituted nicotinamides and nicotinethioamides and N-substituted nicotinamides and nicotinthioamides, 3-acetylpiridine and sodium nicotinate. In one particular embodiment of the invention the nicotinamide moiety is nicotinamide.

Nicotinamide or nicotinamide moiety concentrations suitable for use in some embodiments of the present invention are typically in the range of about 0.5 mM to about 50 mM, about 1.0 mM to about 25 mM, about 1.0 mM to about 25 mM, about 2.5 mM to about 10 mM, about 5.0 mM to about 10 mM. Exemplary effective concentrations of nicotinamide can be of about 0.5 to about 15 mM, 1.0-10.0 mM, typically 2.5 or 5.0 mM, based on the effect of these concentrations of nicotinamide on proliferation and NK cell function. According to some embodiments of the invention, nicotinamide is provided at a concentration in the range (mM) of about 0.5, about 0.75, about 1.0, about 1.25, about 1.5, about 1.75, about 2.0, about 2.25, about 2.5, about 2.75, about 3.0, about 3.25, about 3.5, about 3.75, about 4.0, about 4.25, about 4.5, about 4.75, about 5.0, about 5.25, about 5.5, about 5.75, about 6.0, about 6.25, about 6.5, about 6.75, about 7.0, about 7.25, about 7.5, about 7.75, about 8.0, about 8.25, about 8.5, about 8.75, about 9.0, about 9.25, about 9.5, about 9.75, about 10.0, about 11.0, about 12.0, about 13.0, about 14.0, about 15.0, about 16.0, about 17.0, about 18.0 and about 20.0 mM. All effective intermediate concentrations are contemplated. In specific embodiments, conditions allowing proliferation comprise between 1.0 to 10.0 mM nicotinamide. In yet other embodiments, conditions allowing proliferation comprise 5.0 mM nicotinamide.

Suitable concentrations of the nicotinamide and/or nicotinamide moiety can be determined according to any assay of NK proliferation and/or activity, for example, cell culture or function. Suitable concentration of nicotinamide is a concentration which use thereof in culture "enhances", or results in a net increase of proliferation and/or function of NK cells in culture, compared to "control" cultures having less than 0.1 mM of the nicotinamide and tested from the same NK cell source (e.g. cord blood, bone marrow or peripheral blood preparation), in the same assay and under similar culture conditions (duration of exposure to nicotinamide, time of exposure to nicotinamide).

In some studies, ex-vivo expansion of purified NK cells by culture with nutrients, serum, cytokines and nicotinamide does not require replenishing the medium or manipulation over the culture period, while other studies have advocated culture medium replenishment ("re-feeding") at different intervals during the NK cell culture. In certain embodiments of the present invention, the NK cell fraction is "re-fed" during the culture period. Thus, in specific embodiments, preparing the transplantable NK cell fraction for transplantation comprises supplementing the CD3-depleted NK cell fraction with fresh nutrients, serum, IL-15 and nicotinamide 8-10 days following initiation of the ex-vivo culture (step (b)). In some embodiments, supplementing is provided between 8-9 days following initiation of the ex-vivo culture, between 9-10 days following initiation of the ex-vivo culture, or between 8-10 days following initiation of culturing of the CD3-depleted NK cells. In some embodiments, supplementing (or "refeeding") comprises removing about 30-80%, about 40-70% or about 45-55% of the medium of the NK cell fraction culture, and replacing that with a similar (e.g. equivalent) volume of fresh medium having the same composition and level of nutrients, serum, cytokines (e.g. IL-15) and nicotinamide as the removed medium. In some embodiments, supplementing (or "refeeding") comprises removing about 50% of the medium of the NK cell fraction culture, and replacing the removed medium with a similar (e.g. equivalent) volume of fresh medium having the same composition and level of nutrients, serum, cytokines (e.g. IL-15) and nicotinamide. In other embodiments, culture volume following refeeding reaches approximately twice the original culture volume at initiation of the NK cell culture ("seeding").

NK cell populations can be cultured using a variety of methods and devices. Selection of culture apparatus is usually based on the scale and purpose of the culture. Scaling up of cell culture preferably involves the use of dedicated devices. Apparatus for large scale, clinical grade NK cell production is detailed, for example, in Spanholtz et al. (PLoS ONE 2010; 5:e9221) and Sutlu et al. (Cytotherapy 2010, Early Online 1-12). In some embodiments, culturing the NK cell fractions (e.g. steps (b) and/or (c) of the method) is effected in flasks, at a cell density of $100\text{-}4000 \times 10^6$ cells per flask. In specific embodiments, culturing the NK cell fractions (e.g. initiation of the ex-vivo culture and/or "re-feeding") is effected in flasks, at a cell density of $200\text{-}300 \times 10^6$ cells per flask. In certain embodiments, the flasks are flasks comprising a gas-permeable membrane, such as the G-Rex culture device (G-Rex 100M or closed system G-Rex MCS, WolfWilson, St Paul MN).

It will be appreciated that the density of cells in the culture flask increases with proliferation of the cells over the duration of the culture. Thus, in some embodiments, over the course of expansion in culture, the NK cells of the NK cell fraction are cultured at a cell density of $100\text{-}4000 \times 10^6$ cells per flask, $100\text{-}4000 \times 10^6$ cells per flask, $100\text{-}4000 \times 10^6$ cells per flask, $100\text{-}4000 \times 10^6$ cells per flask, $200\text{-}3000 \times 10^6$ cells per flask, $300\text{-}2000 \times 10^6$ cells per flask, $400\text{-}1000 \times 10^6$ cells per flask, $250\text{-}800 \times 10^6$ cells per flask, $100\text{-}600 \times 10^6$ cells per flask or $150\text{-}500 \times 10^6$ cells per flask. In specific embodiments, over the duration of culture in the flasks, the NK cells of the NK cell fraction are cultured at a cell density of $100\text{-}3000 \times 10^6$ cells per flask.

Culturing the NK cells can be effected with or without feeder cells or a feeder cell layer. Feeder layer-free ex-vivo culture is highly advantageous for clinical applications of cultured cells, including NK cells. Thus, according to one embodiment, culturing the population of NK cells is effected without feeder layer or feeder cells.

In certain embodiments, the CD3-depleted NK cells are harvested from the culture 14-16 days following initiation of the NK cell culture (step (b)). Harvesting of the cells can be performed manually, by releasing attached cells (e.g. "scraping" culture vessel surfaces) or by a cell harvesting device, which is designed to efficiently wash cells out of their culture vessels and collect the cells automatically. In specific embodiments, the expanded CD3-depleted NK cell fraction is harvested from the culture vessels by a cell harvesting device (e.g. the harvesting device of the G-Rex MCS, WolfWilson, St Paul MN).

In some embodiments, harvesting of expanded NK cell fraction from culture removes most, or nearly all of the cells from the culture vessel. In other embodiments, harvesting can be performed in two or more steps, allowing the unharvested cells to remain in culture until harvested at a later time. In certain embodiments, the expanded CD3-depleted NK cell fraction is harvested in two steps, comprising harvesting a first portion of the expanded CD3-depleted NK cell fraction, and then harvesting a second portion of the expanded CD3-depleted NK cell fraction. Harvesting the two portions can be performed with an interval of hours, days or more between harvesting of the first and second portion. The two portions harvested can comprise approximately equal portions of the culture (e.g. equal amounts of the cultured NK cells), or one of the portions may be comprise a larger fraction of the cultured NK cells than the other). In certain embodiments, harvesting comprises harvesting a first portion of the expanded CD3-depleted NK cells about 14 days following step (b)(initiation of culturing), and harvesting a second portion of the expanded CD3-depleted NK cell fraction about 2 days later. In a specific embodiment, the first portion is harvested 14 days following initiation of the ex-vivo culture and the second portion is harvested 16 days following initiation of the ex-vivo culture.

In certain embodiments, the first and second portions are approximately equal, namely, the first (harvested) portion comprises about 50% of the expanded CD3-depleted NK cell fraction and the second (harvested) portion comprises the remainder of the expanded CD3-depleted NK cell fraction.

In order to prepare the expanded CD3-depleted NK cell fraction for transplantation, the harvested cells need to be washed of culture medium, critical parameters evaluated and volume adjusted to a concentration suitable for infusion over a clinically reasonable period of time.

Following harvesting, the expanded CD3-depleted NK cell fraction can be washed free of culture medium manually or, preferably for clinical applications, using an automated device employing a closed system. Washed cells can be reconstituted with an infusion solution (for example, one exemplary infusion solution comprises 8% w/v HSA and 6.8% w/v Dextran-40). In some embodiments, the reconstitution is performed in a closed system. In some embodiments, the infusion solution is screened for suitability for use with the methods and compositions of the present invention. Exemplary criteria for selection of suitable infusion solution include safety tests indicating no bacterial, yeast or mold growth, endotoxin content of less than 0.5 Eu/ml and a clear, foreign particle-free appearance.

As used herein, the term "propagation" or "proliferation" refers to growth, for example, cell growth, and multiplication of cell numbers. Propagation and proliferation, as used herein relate to increased numbers of NK cells accruing during the incubation period. Propagation in vitro or in vivo of cells displaying the phenotype of NK cells is a known phenomenon following their stimulation, for example with IL-2, Epstein-Barr virus-transformed lymphoblastoid lines and others.

Assays for cell proliferation well known in the art, including, but not limited to clonogenic assays, in which cells are seeded and grown in low densities, and colonies counted, mechanical assays [flow cytometry (e.g., FACS™), propidium iodide], which mechanically measure the number of cells, metabolic assays (such as incorporation of tetrazolium salts e.g., XTT, MTT, etc.), which measure numbers of viable cells, direct proliferation assays (such as bromodeoxyuridine, thymidine incorporation, and the like), which measure DNA synthesis of growing populations. In one embodiment, cell proliferation of populations of NK cells cultured with an effective concentrations of nicotinamide and/or other nicotinamide moiety according to the present invention is measured at a predetermined time after seeding NK cells in culture (for example, about 10 hours, 12 hours, about 1, 2, 3, 4, 5, 6, 7 days, about 1, 2, 3, 4, 5 weeks, 2 months or more) is determined by FACS analysis, using anti-CD56 and anti-CD3 markers to identify and quantitate the CD56+CD3− NK cell fraction of the population. Proliferation of NK cells can be expressed as the fold increase, (e.g., expansion or fold expansion) of NK cells, as compared to the original NK cell fraction before culture. In some embodiments, populations of NK cells exposed to effective concentrations of nicotinamide according to the present invention have a fold increase of the NK cell population of at least 2×, at least 10×, at least 20×, at least 40×, at least 50×, at least 75×, at least 100×, at least 150×, at least 250× and at least 500× or more, after about 5, about 7, about 12, about 14, about 16, about 18, about 21, about 25, about 30 or more days culture. In another embodiment, the fold expansion of populations of NK cells, as determined by FACS™, exposed to effective concentrations of nicotinamide is at least about 1.2×, about 1.3×, about 1.5×, about 1.75×, about 2×, about 2.25×, about 2.5×, about 2.75×, about 3.0, about 3.5×, about 4×, about 4.5×, about 5×, about 6×, about 7×, about 8×, about 9×, about 10×, more than that of NK cells cultured in identical conditions with less than 0.1 mM nicotinamide and/or other nicotinamide moiety.

As used herein, the term "function" or "NK cell function" refers to any biological function ascribed to NK cells. A non-limiting list of NK cell functions includes, for example, cytotoxicity, induction of apoptosis, cell motility, directed migration, cytokine and other cell signal response, cytokine/ chemokine production and secretion, expression of activating and inhibitory cell surface molecules in-vitro, cell homing and engraftment (in-vivo retention) in a transplanted host, and alteration of disease or disease processes in vivo. In some embodiments, NK cell functions enhanced by exposure to nicotinamide and/or other nicotinamide moiety include at least one of elevated expression of CD62L surface marker, elevated migration response, and greater cytotoxic activity of the NK cells, as well as elevated homing and in-vivo retention of infused NK cells.

Assays for adhesion and migration molecules such as CD62L, CXCR-4, CD49e and the like, important for homing/engraftment and retention of cells in transplantation, are well known in the art. CD62L expression in a cell can be assayed, for example, by flow cytometry, immunodetection, quantitative cDNA amplification, hybridization and the like. In one embodiment, CD62L expression is detected in different populations of NK cells by exposure of the cells to a fluorescent-tagged specific anti-human CD62L monoclonal antibody [e.g., CD62L PE, Cat. No. 304806 from BioLegend (San Diego, CA, USA)], and sorting of the cells by fluorescent activated cell sorting (FACS).

Assays for cells migration are well known in the art. Migration of cells can be assayed, for example, by transmigration assays or gap closure assays. In transmigration assays, such as the two-chamber technique, cells are separated from a stimulus by a barrier (e.g., filter), and migration of the cells is detected by counting loss of cells from the origin, accumulation of cells across the barrier, or both, at specific intervals. In the gap closure assay, cells are placed on the periphery of a visible gap (scored agar plate, around a circle, etc.) and incubated with a stimulus. Closure of the space between the cells applied by cell motility, in response to a stimulus, is visualized using cytometry, immunodetection, microscopy/morphometrics, etc. In one embodiment, migration potential of different populations of NK cells is determined by the "Transwell" ™ transmigration assay, in response to SDF (250 ng/ml).

Assays for homing and in-vivo retention of transfused or transplanted cells are well known in the art. As used herein, the term "homing" refers to the ability of a transfused or transplanted cell to reach, and survive, in a host target organ. For example, NK cells target organs can be the lymphoid tissue, hepatocytes target organs can be liver parenchyma, alveolar cells target organs can be lung parenchyma, etc. As used herein, the term "in-vivo retention" (also known as "engraftment") refers to the ability of the transfused or transplanted cells to proliferate and remain viable in the target organs. Animal models for assaying homing and in-vivo retention of transplanted NK cells include, but are not limited to immunodeficient small mammals (such as SCID and IL2Rγ$^{null}$ mice and the like). The SCID-Hu mouse model employs C.B-17 scid/scid (SCID) mice transplanted with human fetal thymus and liver tissue or fetal BM tissue and provides an appropriate model for the evaluation of transplanted human NK cells retention and therapeutic potential. Homing and in-vivo retention of transplanted cells can be assessed in human host subjects as well. In one embodiment, homing and in-vivo retention is assayed in irradiated NOD/SCID mice, transfused with, for example, about $15 \times 10^4$, about $15 \times 10^5$, about $15 \times 10^6$, about $15 \times 10^7$ or more human NK cells cultured with an effective concentrations of nicotinamide according to the present invention, and sacrificed at a predetermined time post transfusion (for example, about 5 hours, 10 hours, 12 hours, 1, 2, 3, 4, 5, 6, 7 days, 1, 2, 3, 4, 5 weeks, 2, 3, 4 months or more post transfusion). Upon sacrifice of the mice, samples of spleen, bone marrow, peripheral blood, and other organs are evaluated by FACS for the presence of human NK cells (CD56+ CD45+) using human specific Abs. Percent in vivo retention is expressed as the percent of cells of the organ displaying the donor phenotype (e.g., CD45 for human cells).

Assays for cytotoxicity ("cell killing") are well known in the art. Examples of suitable target cells for use in redirected killing assays are cancer cell line, primary cancer cells solid tumor cells, leukaemic cells, or virally infected cells. Particularly, K562, BL-2, colo250 and primary leukaemic cells can be used, but any of a number of other cell types can be used and are well known in the art (see, e.g., Sivori et al.

(1997) J. Exp. Med. 186: 1129-1136; Vitale et al. (1998) J. Exp. Med. 187: 2065-2072; Pessino et al. (1998) J. Exp. Med. 188: 953-960; Neri et al. (2001) Clin. Diag. Lab. Immun. 8:1131-1135). Cell killing is assessed by cell viability assays (e.g., dye exclusion, chromium release, CFSE), metabolic assays (e.g., tetrazolium salts), and direct observation.

Once the expanded CD3-depleted NK cell fraction has been washed and concentrated, the expanded fraction can be evaluated for suitability for use in transplantation. Typical criteria for selection of suitable transplantable NK cell fractions include the percentage of CD56+/CD3− cells, cell viability, size of the CD3+ cell fraction, presence of endotoxin, microbial contamination and the like. It will be noted that the CD56+, CD3+ and CD56+/CD3− cell content of the expanded NK cell fraction is critical to the successful engraftment of the transplanted NK cells, and is thus a central criterion for proceeding to ex-vivo expansion. Thus, in particular embodiments, the washed and concentrated expanded NK cell fraction generated by step (e) of the method of the invention is characterized by about 60% to about 90% CD56+/CD3− cells, about 68% to about 85% CD56+/CD3− cells, about 72% to about 82% CD56+/CD3− cells and about 76-79% CD56+/CD3− cells. In one embodiment, the washed and concentrated expanded NK cell fraction generated by step (e) of the method of the invention is characterized by at least 60%, at least 64%, at least 70%, at least 74%, at least 80% or at least 85% CD56+/CD3− cells. In a further embodiment, the washed and concentrated expanded NK cell fraction generated by step (e) of the method of the invention is characterized by at least 70% CD56+/CD3− cells. Identification of NK cells phenotype according to CD56 and CD3 cell markers is described in detail hereinabove.

The presence of allogeneic T (CD3+) cells in cell fractions intended for transplantation is problematic, since they strongly increase the risk of GVHD. Thus, an important parameter for suitability of transplantable expanded NK cell fractions is the amount or fraction of CD3+ cells. Thus, in particular embodiments, the washed and concentrated expanded NK cell fraction generated by the methods of the invention is characterized by between $1.0 \times 10^5$ and $1.0 \times 10^6$ CD3+ cells per Kg mass of the patient. In further embodiments, the washed and concentrated expanded NK cell fraction generated by the methods of the invention is characterized by fewer than $7.0 \times 10^5$ CD3+ cells per Kg mass of the patient, fewer than $6.5 \times 10^5$ CD3+ cells per Kg mass of the patient, fewer than $6.0 \times 10^5$ CD3+ cells per Kg mass of the patient, fewer than $5.5 \times 10^5$ CD3+ cells per Kg mass of the patient, fewer than $5.0 \times 10^5$ CD3+ cells per Kg mass of the patient, fewer than $4.5 \times 10^5$ CD3+ cells per Kg mass of the patient, fewer than $4.0 \times 10^5$ CD3+ cells per Kg mass of the patient, fewer than $3.5 \times 10^5$ CD3+ cells per Kg mass of the patient or fewer than $3.0 \times 10^5$ CD3+ cells per Kg mass of the patient. In one embodiment, the washed and concentrated expanded NK cell fraction generated by the methods of the invention is characterized by fewer than $7.0 \times 10^5$ CD3+ cells per Kg mass of the patient. It will be noted that calculation of the CD3+ fraction, portion or content of the washed and concentrated expanded NK cell fraction generated by the method of the invention, expressed per Kg mass of the patient, relates to the total amount of CD3+ cells transplanted (e.g. infused) into the patient (i.e. subject). The fraction, portion or amount of CD3+ cells in the washed and concentrated expanded NK cell fraction generated by step (e) of the method of the invention can also be expressed as a ratio of CD56+/CD3− to CD3+ cells, or as a volume fraction (e.g. CD3+ cells/mL) or weight fraction (CD3+ cells/100 g) of the washed and concentrated expanded NK cell fraction generated by the methods of the invention. Identification of CD3+ cell markers is described in detail hereinabove.

Sterility and safety of the expanded, CD3-depleted NK cell fractions for transplantation is assured by monitoring, inter alia, the endotoxin content and presence of bacterial, fungal, viral and mycoplasma contamination. In some embodiments, the expanded NK cell fraction selected for transplantation has an endotoxin content of no more than 5 Eu/ml after washing and concentration. In some embodiments, the expanded NK cell fraction for transplantation is characterized as being free of microorganisms (for example, Gram-positive microorganisms) following washing and concentration.

In some embodiments, the expanded NK cell fraction suitable for transplantation is characterized by about 50% to about 85% viability. In some embodiments, expanded NK cell fractions having about 55%, about 60%, about 63%, about 65%, about 68%, about 70%, about 75%, about 78%, about 80%, about 82%, about 83%, about 84% to about 85% viability or greater are selected. In a further embodiment, the NK cell fraction selected for ex-vivo expansion has at least 70% viable cells. In a further embodiment, the expanded NK cell fraction suitable for transplantation is characterized by at least 70% viable cells following washing and concentration. In a further embodiment, the expanded NK cell fraction suitable for transplantation has at least 85% viable cells.

As used herein, the term "viability" refers to the distinction between living and non-living cells. Cell viability may be judged by morphological changes or by changes in membrane permeability and/or physiological state inferred from the exclusion of certain dyes or the uptake and retention of others. Cell viability assessment is well known in the art, including, but not limited to assays (e.g., dye exclusion, chromium release), metabolic assays (e.g., tetrazolium salts), and direct observation. (Coder, D., Current Protocols in Cytometry, 1997, John Wiley and Sons, Inc., Unit 9.2, 9.2.1-9.2.14).

In some embodiments, the parameters of CD56+/CD3− cell fraction, CD3+ cells fraction, viability, endotoxin and microorganism content are monitored in samples drawn prior to NK cell culture, during NK cell culture, after harvesting of the first and/or second portions, and/or following wash and concentration of the expanded NK cell fractions. In some embodiments, the samples are drawn from any of the apheresis unit before processing ($100 \times 10^6$ cells), post-column (CD3 depletion) pre culture sample ($10 \times 10^6$ cells), post-expansion-pre-wash (10 ml sample), final expanded, washed and concentrated NK cell product ($10 \times 10^6$ cells) on the day of first infusion (Day 0) and the final expanded, washed and concentrated NK cell product ($10 \times 10^6$ cells) on the day of the second infusion (Day +2), or any combination thereof.

Thus, according to specific embodiments, the washed and concentrated expanded NK cell fraction generated by the method of the present invention is characterized by the following parameters:

(a) at least 70% CD56+/CD3− cells;
(b) at least 70% viability;
(c) fewer than $5.0 \times 10^5$ CD3+ cells/Kg mass of patient, upon infusion;
(d) no more than 5 EU endotoxin/Kg mass of patient, upon infusion; and
(e) no Gram-positive micro-organisms.

Expanded CD3-depleted NK cell fractions meeting the abovementioned criteria by can be used for transplantation into subjects (e.g. patients) in need thereof. Any of the methods for ex-vivo expansion (culturing), selection and preparation of NK cell fractions for transplantation described hereinabove, and each of their embodiments taken alone or in various combinations may be used for affecting the methods for transplanting expanded NK cell fractions as is described in this section and the sections that follow.

Thus, in some embodiments, there is provided a transplantable NK cell fraction prepared according to any of the methods for preparing a transplantable NK cell fraction described herein. In specific embodiments, the transplantable NK cell fraction is characterized by the following parameters:
 (a) at least 70% CD56+/CD3− cells;
 (b) at least 70% viability;
 (c) fewer than $5.0 \times 10^5$ CD3+ cells/Kg mass of patient, upon infusion;
 (d) no more than 5 EU endotoxin/Kg mass of patient, upon infusion; and
 (e) no Gram-positive micro-organisms.

In some embodiments, following wash and concentration, the transplantable NK cell fraction is transferred to a container (e.g. for transfer to the site of transplantation (infusion)). In some embodiments, the container is a culture bag. Culture bags constructed of inert materials, having high gas permeability and low water loss, flexibility and high optical transmission are desirable. In specific embodiments, the transplantable expanded NK cell fraction is provided in a fluorinated ethylene propylene (FEP) culture bag.

In other embodiments, there is provided a transplantable human NK cell fraction characterized by the following parameters:
 (a) at least 70% CD56+/CD3− cells;
 (b) at least 70% viability;
 (c) fewer than $5.0 \times 10^5$ CD3+ cells/Kg mass of patient, upon infusion;
 (d) no more than 5 EU endotoxin/Kg mass of patient, upon infusion; and
 (e) no Gram-positive micro-organisms.

Expanded NK cell fractions of the invention can be used for transplantation into subjects in need thereof.

As used herein, the term "transplantation", in the context of cell therapy, adoptive transfer, cellular immunotherapy or the like refers to administration of cells having an expected therapeutic effect to a subject, preferably to a subject in need thereof, for example, as treatment of a patient for a disease or condition. Since such cell therapy comprises introduction of the therapeutic cell fraction into the subject's body via a vascular connection, as used herein, "transplantation" and "administration" of NK cells is equivalent to "infusion". Typically, therapeutic cell fractions are infused into the subject intravenously, for example, via a central venous catheter (e.g. Hickman catheter). Rate of infusion of the therapeutic cell fraction into the subject can be controlled by a pump, or unassisted, fed by gravity and adjusted by the height differential between the cell faction and the entrance catheter. In some embodiments, the expanded NK cell fraction is transplanted (infused, administered) intravenously, by gravity feed, without a pump or pumps and/or without filters.

In some embodiments, the subject in need of transplantation is suffering from a hematological disease. In some embodiments, the subject is suffering from a hematological malignancy. In specific embodiments, hematologic malignancies indicated for treatment with the expanded NK cell fraction or methods described herein are multiple myeloma and non-Hodgkin's lymphoma.

Thus, in some embodiments, there is provided a method of treating a hematological disease in a subject in need thereof, the method comprising:
 (a) administering an anti-cancer monoclonal antibody to the subject;
 (b) administering at least one immunosuppressive agent to the subject;
 (c) transplanting an expanded CD3-depleted haploidentical or mismatched NK cell fraction into the subject in need thereof, wherein the expanded CD3-depleted HLA-haploidentical or HLA-mismatched NK cell fraction has been expanded by ex-vivo culturing with nutrients, serum, IL-15 and nicotinamide in an amount between 1.0 mM to 10 mM; and
 (d) administering IL-2 to said subject,
 thereby treating the hematological disease in the subject.

As used herein, a "subject" or "patient" can be any mammal, e.g., a human, a primate, mouse, rat, dog, cat, cow, horse, pig, sheep, goat, camel. In a specific embodiment, the subject is a human. In further embodiments, the subject is human and the NK cell fraction is a human NK cell fraction.

As used herein, a "subject in need thereof" is a subject having the need for transplantation, transfusion, infusion or implantation of the NK cell fractions of the present invention to treat or ameliorate a disease, disorder or condition. In one embodiment, the subject has (been diagnosed with) or suffering from a hematological disease. In some embodiments, the hematological disease is a cell proliferative disorder. In other embodiments, the hematological disease is a hematological malignancy.

As used herein, the term "risk of" or "probability of" refers to the likelihood of an occurrence. In some embodiments, the risk or probability of an occurrence (e.g engraftment or non-engraftment of NK cell fraction, non-relapse mortality, and the like) in an individual refers to a risk calculated from comparative data between groups receiving treatment compared to groups not receiving the same treatment. In some embodiments, an increased or decreased risk or probability reflects the difference between treatment and control groups with respect to the outcome under consideration. In some embodiments, an increase or decrease in the risk or probability of a particular occurrence or condition is only relative, and not expressed in numerical values.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. In specific embodiments, the methods provided herein are used to treat or alleviate a symptom of cancer. The term "cancer" includes solid tumors, as well as, hematologic tumors and/or malignancies. In specific embodiments, the hematological malignancy is non-Hodgkin's lymphoma (NHL) or multiple myeloma (MM).

In some embodiments, the methods and compositions and kits of the present invention can be used for treatment of subjects of all age groups. In specific embodiments, the subject or patient is greater than 18 and fewer than 70 years of age.

In some embodiments, the subject in need thereof can have multiple myeloma. In further embodiments, the multiple myeloma is (MM) characterized by at least one of the following criteria: (a) relapsed disease between 2-18 months following first autologous stem cell transplantation, (b) relapsed disease at least 4 months following allogeneic stem cell transplantation with no evidence of active graft versus host disease (GVHD), (c) relapsed/refractory disease following at least two lines of therapy including proteasome inhibitor and an immunomodulatory drug (IMiD), (d) Serum IgG, IgA, IgM or IgD Myeloma protein (M-protein) greater than or equal to 0.5 g/dL and (e) Urine M-protein greater than or equal to 200 mg/24 collection. In some embodiments, the multiple myeloma is also characterized by serum IgE Myeloma protein (M-protein) greater than or equal to 0.5 g/dL, and has undergone plasmapheresis no fewer than 4 weeks prior to the start of NK treatment. In some embodiments, the subject in need thereof has multiple myeloma characterized by more than one of the criteria described herein.

The subject in need thereof can have Non-Hodgkin's lymphoma (NHL). In some embodiments, the Non-Hodgkin's Lymphoma is a CD20 positive B cell NHL, with CD20 expression confirmed by flow cytometry or immunohistochemistry. In further embodiments, the NHL is characterized by at least one of the following features: (a) relapsed/refractory disease that has failed conventional therapy, (b) relapsed disease at least 60 days following autologous stem cell transplantation, (c) relapsed disease at least 4 months following allogeneic stem cell transplantation with no evidence of active graft versus host disease, and (d) measurable disease greater than or equal to 1.5 cm in diameter. In some embodiments, the subject in need thereof has NHL characterized by more than one of the criteria described herein.

In some embodiments, a subject in need thereof can be further defined according to the following criteria: a performance score of at least 60% by Karnofsky, and adequate organ function defined as: a. Cardiac function: Left ventricular ejection fraction (LVEF) of ≥40% by echocardiogram, radionuclide scan or cardiac MRI; b. Pulmonary function: Oxygen saturation at least 90% on room air, pulmonary function tests demonstrating FVC and FEV1 of ≥50% of predicted for age and cDLCO≥50% of predicted; c. Renal function: Creatinine clearance test (by Cockcroft-Gault equation)≥40 mL/min or creatinine≤1.5 mg/dL, d. Hepatic function: Total Serum Bilirubin≤1.5× upper limit of institutional norm, Hepatic transaminases (ALT and AST) <3× upper limit of institutional normal range; e. Hematology: Total white blood cell (WBC) count≥3000/μL, absolute neutrophil count (ANC)≥1000/μL, platelet count≥75,000/μL and hemoglobin≥8.0 g/dL (may be waived if abnormalities are due to disease related bone marrow involvement), and f. Calcium (for multiple myeloma patients only): Corrected calcium<11.5 mg/dL within 2 weeks prior to enrollment for treatment.

In some embodiments, eligible subjects should be capable of discontinuing prednisone or other immunosuppressive medications for at least 3 days prior to NAM-NK cell infusion (excluding preparative regimen pre-medications). Sexually active females of child bearing potential and males with partners of child bearing potential may be requested to agree to use effective contraception during therapy and for 4 months after completion of therapy.

In some embodiments, subjects can be excluded from consideration for treatment for any of the following:
1. High titer of donor specific anti-HLA antibodies (MFI>1000);
2. Active, untreated CNS involvement;
3. Chronic lymphocytic leukemia (CLL)/small lymphocytic lymphoma (SLL), or high-grade lymphomas (Burkittt's lymphoma/Lymphoblastic lymphoma);
4. Pregnant or breastfeeding;
5. For subjects having multiple myeloma: Women of child bearing potential must have a negative serum or urine pregnancy test (minimum sensitivity 25 IU/L or equivalent units of HCG) within 14 days of initiation of treatment (24 hours prior to the start of anti-cancer antibody administration);
6. Marked baseline prolongation of QT/QTc interval (e.g. demonstration of a QTc interval greater than 500 milliseconds);
7. Class II or greater New York Heart Association Functional Classification criteria (appendix III) or serious cardiac arrhythmias likely to increase the risk of cardiac complications of cytokine therapy (e.g. ventricular tachycardia, frequent ventricular ectopy, or supraventricular tachyarrhythmia requiring chronic therapy);
8. Active autoimmune disease requiring immunosuppressive therapy;
9. History of severe asthma, presently on chronic medications (a history of mild asthma requiring inhaled steroids only is eligible);
10. New or progressive pulmonary infiltrates on screening chest x-ray or chest CT scan [unless cleared for study by a pulmonary specialist. Infiltrates attributed to infection must be stable/improving (with associated clinical improvement) after 1 week of appropriate therapy (4 weeks for presumed or documented fungal infections)];
11. Active uncontrolled bacterial, fungal, or viral infections—all prior infections must have resolved following optimal therapy;
12. Known hypersensitivity to any of the therapeutic agents used in the methods of the invention;
13. For MM patients only: Prior radiotherapy within 2 weeks prior to the administration of the NK cell fraction of the invention, surgery within 4 weeks or chemotherapy within 3 weeks (6 weeks for melphalan, or monoclonal antibodies);
14. Received investigational drugs within the 14 days before initiation of treatment with NK cell fraction;

In some embodiments, NK cell donors (for example, candidates for apheresis, identified as HLA-haploidentical or HLA-mismatched, related or non-related) are selected according to the following criteria:
1. HLA-haploidentical or mismatched related donor/recipient match based on a minimum of intermediate resolution DNA based Class I typing of the A and B locus (at least 2/4 class I allele) and absence of (MFI≤1000) recipient anti HLA antibodies against the selected donor;
2. 12 to 70 years of age—Priority should be given to age (<35 years), followed by HLA matching (haploidentical and if not available then fully mismatched donor);
3. At least 40 kilogram body weight;
4. In general good health as determined by an evaluating medical provider;
5. Adequate organ function defined as: Hematologic: hemoglobin, WBC, platelet within 10% of upper and lower limit of normal range of test (gender based for hemoglobin), Hepatic: ALT<2× upper limit of normal and Renal: serum creatinine<1.8 mg/dL;
6. Completion of a donor infectious disease screen panel including CMV Antibody, Hepatitis B Surface Antigen, Hepatitis B Core Antibody, Hepatitis C Antibody, HIV PCR, HIV/2 Antibody, HTLVA ½ Antibody, Rapid Plasma (RPR) *Treponema, Trypanosoma cruzi* (*T. cruzi*), HCV by NAT, HIV by NAT and WNV (West Nile Virus) by NAT or per current panel—must be negative for HIV and active hepatitis B;
7. Not pregnant—females of childbearing potential must have a negative pregnancy test within 7 days of apheresis;
8. Able and willing to undergo apheresis;
9. Voluntary written consent (using assent form if donor<18 years of age).

In some embodiments, the subject in need thereof receives myeloablative therapy or conditioning regime. In specific embodiments, the subject is subjected to myeloablative therapy or conditioning regime prior to, concomitant with and following transplantation or administration of the compositions of the present invention. The myeloablative therapy or conditioning regime can include total body irradiation (TBI), immunotherapy, and chemotherapy and/or immunosuppressive therapy.

In order to facilitate tumor targeting and antibody dependent cellular cytotoxicity (ADCC), in some embodiments, disease specific monoclonal antibodies can be administered to the subject in need thereof. Thus, in some embodiments, wherein the hematological malignancy is multiple myeloma, one or more MM-specific monoclonal antibodies (such as elotuzumab) is administered to the subject in need thereof. An exemplary dosage of elotuzumab useful for the method of the invention is 10 mg/Kg weight of the subject (patient). Wherein the hematological malignancy is NHL, one or more NHL-specific monoclonal antibodies (such as rituximab) is administered to the subject in need thereof. An exemplary dosage of rituximab useful for the method of the invention is 375 mg/m² of the subject (patient). In specific embodiments, disease-specific monoclonal antibody treatment comprises administration of the monoclonal antibody(s) in three doses: first dose 10 days prior to administration (infusion, transplantation) of the NK cell fraction, second dose three days prior to administration (infusion, transplantation) of the NK cell fraction and third, and last dose 11 days following administration (infusion, transplantation) of the NK cell fraction, and in some embodiment, approximately 1 week following administration (infusion, transplantation) of the final (second) NK cell fraction. In certain embodiments, the disease specific monoclonal antibody is administered at 9-11 days before the first dose, at 3 days before the first dose and at 11 days following the first dose of expanded CD3-depleted haploidentical or mismatched NK cell fraction.

Standard guidelines for infusion, monitoring reactions and toxicities to monoclonal antibody administration are followed. Elotuzumab is typically administered along with a premedication regimen including dexamethasone, an H1 blocker such as diphenylhydramine, an H2 blocker such as ranitidine and acetaminophen prior to start of the infusion.

In some embodiments, the subject in need thereof receives a preparative regime of immunosuppressive therapy prior to administration (infusion, transplantation) of the NK cell fraction. Suitable immunosuppressive agents include, but are not limited to alkylating agents, purine analogs, antimetabolites, and the like. Some immunosuppressive agents are also considered chemotherapeutic immunosuppressive agent. In specific embodiments, the immunosuppressive therapy comprises administration of cyclophophamide and fludarabine. An exemplary dosage of cyclophosphamide useful for the method of the invention is 40 mg/Kg weight of the subject (patient), and an exemplary dosage of fludarabine useful for the method of the invention is 25 mg/m² of the subject (patient). In specific embodiments, cyclophosphamide is administered 5 days prior to administration (transplantation, infusion) of expanded CD3-depleted HLA-haploidentical or HLA-mismatched NK cells, and the fludarabine is administered on each one of days 5, 4 and 3 prior to administration (transplantation, infusion) of the expanded CD3-depleted HLA-haploidentical or HLA-mismatched NK cells. Alternatively, fludarabine and cyclophosphamide administration can be adjusted such that the last dose of the immunosuppressive agent is completed 2 or 3 days prior to initiation of NK cell fraction administration.

According to the methods of the present invention, in some embodiments, the NK cell fraction is administered into the subject in need thereof in two doses. In specific embodiments, administering the NK cell fraction comprises administering a first dose of expanded CD3-depleted HLA-haploidentical or HLA-mismatched NK cell fraction, followed two days later by a second dose of the expanded CD3-depleted HLA-haploidentical or HLA-mismatched NK cell fraction.

In some embodiments, the NK cell fraction for administration to the subject (patient) comprises between $1\times10^7$/kg and $5\times10^8$/kg, between $2\times10^7$/kg and $2\times10^8$/kg, between $5\times10^7$/kg and $1\times10^8$/kg, or between $2\times10^7$/kg and $5\times10^7$/kg expanded CD3-depleted HLA-haploidentical or HLA-mismatched NK cells. In some embodiments, the combined said first and said second doses of NK cell fraction comprise $2\times10^7$/kg to $2\times10^8$/kg total expanded CD3-depleted HLA-haploidentical or HLA-mismatched NK cells. In some embodiments, the first dose and second dose of the NK cell fraction each comprise $1\times10^7$/kg expanded CD3-depleted haploidentical or mismatched NK cells, for a total dose of $2\times10^7$/kg expanded CD3-depleted haploidentical or mismatched NK cells. In other embodiments, the first dose and the second dose of the NK cell fraction each comprise $5\times10^7$/kg expanded CD3-depleted haploidentical or mismatched NK cells, for a total dose of $1\times10^8$/kg expanded CD3-depleted haploidentical or mismatched NK cells. In yet another embodiment, the first dose and the second dose of the NK cell fraction each comprise $1\times10^8$/kg expanded CD3-depleted haploidentical or mismatched NK cells, for a total dose of $2\times10^8$/kg expanded CD3-depleted haploidentical or mismatched NK cells.

Administration of NK cell fraction is typically performed as an inpatient procedure. Administration of NK cell fractions described herein is by infusion, and in specific embodiments, NK cell fractions are infused into the subject (patient) within 1 hour of arrival of the transplantable NK cell fraction and no later than 10 hours after final product release of the washed and concentrated expanded CD3-depleted NK cell fraction. In specific embodiments, the washed and concentrated expanded CD3-depleted NK cell fraction is maintained, until administration, at room temperature, and is not refrigerated before use.

Thus, in some embodiments, the expanded CD3-depleted HLA-haploidentical or HLA-mismatched NK cell fraction is administered to the subject no more than 1 hour later after provision of the NK cell fraction for transplantation and no more than 10 hours following final product release of the NK cell fraction. In some embodiments, the expanded CD3-depleted haploidentical or mismatched NK cell fraction is administered to the subject by intravenous infusion, without a filter or pump, for a duration of no less than 15 and no more than 60 minutes per infusion.

In some embodiments, the subject in need thereof receives a supportive regimen of interleukin 2 (IL-2) following NK cell fraction administration.

In some embodiments, IL-2 is administered subcutaneously (SC) at a dosage of 6 MU (for patients weighing <45 kilograms, the IL-2 dosage is 3 MU/m$^2$) on the day of the initial NK cell fraction administration (transplantation, infusion), on the day of the second NK cell fraction administration (transplantation, infusion) and two days after the second NK cell fraction administration (transplantation, infusion), for a total of 3 doses. In some embodiments, the IL-2 is administered no sooner than 4 hours after the NAM-NK cells on days of the NAM-NK cell infusion. In certain embodiments, the first two IL-2 doses are administered as part of the hospitalization for the NK cell infusion. The third IL-2 dosage may be administered in an outpatient context. Thus, in specific embodiments, 11-2 administration comprises administering 6×10$^6$ units IL-2 following transfusion of expanded CD3-depleted NK cells:

(i) on the day of transfusion of said expanded CD3-depleted HLA-haploidentical or mismatched NK cells, and (ii) two days following transfusion of said expanded CD3-depleted haploidentical or mismatched NK cells, and (iii) four days transfusion of said expanded CD3-depleted haploidentical or mismatched NK cells.

Further, if the patient has experienced grade 2 or greater IL-2 infusion-related toxicity with the first or second dose, the dose of IL-2 may be held for up to 48 hours. If the toxicity resolves to grade 1 or better within the 48 hours, IL-2 may be given with all planned doses to be given; however the administration of remaining dose(s) is to be at least 24 hours apart.

In some embodiments, subjects can receive any or all of the following: infusion support (e.g. diphenylhydramine or dexchlorpheniramine, hydrocortisone and acetaminophen), supportive cytokines (e.g. G-CSF), blood products as needed, anti-viral, anti-bacterial, PCP and/or fungal prophylaxis, CMV, EBV and HHV6 surveillance and IV immunoglobulin as needed.

In some embodiments, subjects receive any or all of an additional treatment for the hematological disease. Said treatment can be a treatment selected from the group consisting of an immunosuppressive treatment, chemotherapy and radio-therapy.

Thus, in some embodiments there is provided a method of treating a hematological disease in a subject in need thereof, the method comprising:

(i) obtaining a CD3-depleted NK cell fraction HLA-haploidentical or HLA-mismatched for the subject;

(ii) ex vivo culturing said CD3-depleted NK cell fraction under conditions allowing for cell proliferation, wherein the conditions comprise providing nutrients, serum, IL-15 and nicotinamide in an amount between 1.0 mM to 10 mM;

(iii) supplementing the CD3-depleted NK cell fraction with fresh nutrients, serum, IL-15 and nicotinamide 8-10 days following step (ii) to produce an expanded CD3-depleted NK cell fraction;

(iv) harvesting the expanded CD3-depleted NK cell fraction 14-16 days following step (ii);

(v) washing and concentrating the expanded CD3-depleted NK cell fraction of step (iv), thereby producing a transplantable NK cell fraction for transplantation in the subject;

(vi) administering an anti-cancer monoclonal antibody to the subject;

(vii) administering at least one immunosuppressive agent to the subject;

(viii) transplanting the expanded CD3-depleted haploidentical or mismatched NK cell fraction of (v) into the subject in need thereof; and (ix) administering IL-2 to the subject, thereby treating the hematological disease in the subject.

In some embodiments, the NK cell fraction infusion solution is stored in bags until use (e.g. transplantation, infusion) at 8-20° C. In some specific embodiments, transplantation (administration, infusion) of the NK cell fraction is preceded by a safety assessment of the subject in need thereof on the day of NK cell transplantation, typically including a physical examination, CBC, blood chemistry (e.g at least serum creatinine, total bilirubin, alkaline phosphatase, AST, ALT and magnesium), Vital Signs: weight, temperature, blood pressure, pulse, and respiratory rate, and administration of concomitant medication, including RBC and platelet transfusions.

Infusion of the expanded NK cell fractions into the subject in need thereof is typically done by infusion via the patient's central venous catheter, subject to the limitations of individual site practice.

The method of treatment of hematological disease of the present invention can be used to treat hematological malignancies, including, but not limited to MM and NHL. As used herein, the term "treating a hematological disease" or "treating a hematological malignancy" refers to reducing the symptoms or signs of the hematological disease. In some embodiments, treating hematological diseases or a hematological malignancy is assessed according to, but not exclusively, reduction in symptoms over time, improvement in clinical parameters, reduced hospitalization and reduced risk of relapse or mortality.

In some embodiments, infusion of expanded NK cell fractions described herein increases the probability of successful in-vivo expansion of the infused NK cells when compared to infusion of NK cells not cultured and/or administered according to the methods described herein. In some embodiments, the success of expansion in-vivo is measured on days 7 and 14 following infusion.

In other embodiments, infusion of expanded NK cell fractions described herein increases the function of the NK cells in the peripheral blood of the subject when compared to infusion of NK cells not cultured and/or administered according to the methods described herein. In some embodiments, NK cells function is measured on days 7 and 14 following infusion.

According to some embodiments of the method of the present invention, infusion of expanded NK cell fractions described herein increases the probability of favorable disease response infusion of the NK cell fraction, when compared to infusion of NK cells not cultured and/or administered according to the methods described herein. In some embodiments, NK cells function is measured on day 28 and at one year following infusion. In specific embodiments, the hematological malignancy is NHL and the disease response criteria for NHL are assessed according to the International Working Group Response Criteria for NHL (for details, see Cheson, et al, J Clin Oncol 2014; 32:3059-68). In further specific embodiments, the hematological malignancy is MM and the disease response criteria for MM are assessed according to the following criteria:

Plasma Cell Leukemia Uniform Response Criteria

Stringent Complete Response (sCR):

sCR requires, in addition to CR (defined below), all of the following:
- Absence of malignant plasma cells in the bone marrow by flow cytometry
- Absence of malignant plasma cells in peripheral blood by flow cytometry
- Normal free light chain ratio (FLC)

Complete Response (CR):

CR requires all of the following:
- Less than 5% plasma cells in a bone marrow aspirate
- Absence of plasma cells in peripheral blood
- Absence of the original monoclonal paraprotein in serum and urine by routine electrophoresis and by immunofixation.
- Absence of extramedullary disease Very Good Partial Remission (VGPR)

VGPR requires all of the following:
- Less than 5% plasma cells in a bone marrow aspirate
- Absence of plasma cells in the peripheral blood
- Greater than or equal to 90% reduction of serum monoclonal paraprotein plus paraprotein<100 mg/24 hrs$^2$
- Absence of extramedullary disease Partial Response (PR)

Partial response requires all of the following:
- Between 5% and 25% plasma cells in a bone marrow aspirate
- Between 1% and 5% plasma cells in the peripheral blood
- Greater than or equal to 50% reduction of serum monoclonal paraprotein and reduction in 24-hour urinary monoclonal paraprotein by greater than or equal to 90% plus less than 200 mg/24 hr$^3$
- Greater than or equal to 50% reduction in the size of extramedullary disease Stable Disease (SD)

Patients who do not meet criteria for sCR, CR, VGPR, PR or progressive disease (defined below) are considered to have stable disease (SD):
- If the serum and urine M-Protein are unmeasurable, a normal serum kappa/lambda FLC ratio is also required.
- If the serum and urine M-Protein are unmeasurable, a greater than or equal to 90% decrease in the difference between involved and uninvolved FLC levels is required instead of the M-Protein.
- If the serum and urine M-Protein are unmeasurable, a great than or equal to 50% decrease in the difference between involved and uninvolved FLC levels is required instead of the M-Protein.

Progressive Disease

Progression from CR or sCR requires one or more of the following:
- >25% increase in the plasma cells in a bone marrow aspirate, or an absolute increase of greater than or equal to 10%
- >5% absolute increase in plasma cells in the peripheral blood
- >25% increase in the level of the serum monoclonal paraprotein with an absolute increase of greater than or equal to 5 g/L
- >25% increase in the 24-hour urine protein electrophoresis with an absolute increase of at least 200 mg/24 hours
- Hypercalcemia
- Definite increase in lytic bone lesions
- Definite increase in the size or number of extramedullary disease.

In some embodiments, the article of manufacture, composition or kit of the present invention further comprises instructions for administering the expanded NK cell fractions suitable for transplantation into a subject in need thereof.

In some embodiments of the article of manufacture, composition or kit of the present invention, the expanded NK cell fractions suitable for transplantation into a subject in need thereof comprises at least $7 \times 10^8$ total viable NK cells. In some embodiments, the expanded NK cell fractions suitable for transplantation into a subject in need thereof comprises at least $8 \times 10^8$ total viable NK cells, at least $10 \times 10^8$ total viable NK cells, at least $15 \times 10^8$ total viable NK cells, at least $20 \times 10^8$ total viable NK cells or at least $25 \times 10^8$ total viable NK cells.

Selected cell populations of the present invention can be provided per se, along with the culture medium containing same, isolated from the culture medium, and combined with a pharmaceutically acceptable carrier as well as with additional agents which may promote cell engraftment and/or organ function (e.g., immunosuppressing agents, antibiotics, growth factor). Hence, cell populations of the invention can be administered in a pharmaceutically acceptable carrier or diluent, such as sterile saline and aqueous buffer solutions. The use of such carriers and diluents is well known in the art.

Compositions of the present invention may, if desired, be presented in a pack or dispenser device, such as an FDA-approved kit or article of manufacture, which may contain one or more unit dosage forms containing the active ingredient (e.g., cells). The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

The cells prepared according to the methods of the present invention can be administered to the subject per se, or in a pharmaceutical composition where it is mixed with suitable carriers or excipients.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Techniques for formulation and administration of drugs may be found in the latest edition of "Remington's Pharmaceutical Sciences," Mack Publishing Co., Easton, PA, which is herein fully incorporated by reference.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g. expanded CD3-depleted NK cells) effective to prevent, alleviate, or ameliorate symptoms of a disorder (e.g., leukemia, multiple myeloma) or prolong the survival of the subject being treated.

Determination of a therapeutically effective amount is well within the capability of those skilled in the art, especially in light of the detailed disclosure provided herein.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity and responsiveness of the condition to be treated, dosing can be of a single or a plurality of administrations. The amount of a composition to be administered will, of course, be dependent on the subject being treated, the severity of the affliction, the manner of administration, the judgment of the prescribing physician, etc.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of preparing a transplantable NK cell fraction for transplantation, in two portions, into a subject in need thereof, wherein the subject is a human subject that is greater than 18 years of age, the method comprising:
    (a) ex vivo culturing a CD3-depleted NK cell fraction HLA-haploidentical or HLA-mismatched for said subject under conditions allowing for cell proliferation, wherein said conditions comprise providing nutrients, serum, IL-15 and nicotinamide in an amount between 1.0 mM to 10 mM;
    (b) supplementing said CD3-depleted NK cell fraction with fresh nutrients, serum, IL-15 and nicotinamide 8-10 days following step (a) to produce an expanded CD3-depleted NK cell fraction;
    (c) harvesting a first portion of said expanded CD3-depleted NK cell fraction 14 days following step (a), and harvesting a second portion of said expanded CD3-depleted NK cell fraction 16 days following step (a), wherein said first portion comprises about 50% of said expanded CD3-depleted NK cell fraction and said second portion comprises the remainder of said expanded CD3-depleted NK cell fraction,
    wherein said first portion and the second portion each comprise at least $1\times10^7$ to $5\times10^8$ NK cells per kg of the subject; and
    (d) washing and concentrating said first and said second portions of said expanded CD3-depleted NK cell fraction of step (c), (e) transferring each of said washed and concentrated first and said second portions of said expanded CD3-depleted NK cell fraction to one or more culture bags, (f) reconstituting each of said washed and concentrated first and said second portions of said expanded CD3-depleted NK cell fraction with an infusion solution, and (g) storing each of the reconstituted first and said second portions of said expanded CD3-depleted NK cell fraction at room temperature until infusion into said subject, wherein said storing is for no later than 10 hours after final product release of each of the first and second portions of said washed and concentrated expanded CD3-depleted NK cell fraction.

2. The method of claim 1, wherein said CD3-depleted NK cell fraction is a human NK cell fraction.

3. The method of claim 1, wherein said ex-vivo culturing is devoid of a feeder layer.

4. The method of claim 1, wherein said conditions for allowing for cell proliferation comprise providing 10% human serum.

5. The method of claim 1, wherein said nutrients comprise minimal essential cell culture medium.

6. The method of claim 1, wherein said NK cell fraction is from an HLA-haploidentical or HLA-mismatched donor having at least:

(a) HLA matching at intermediate resolution DNA-based Class 1 typing of the A and B locus of at least 2/4 class 1 allele; and (b) absence of (MFI <1000) recipient donor-specific anti-HLA antibodies, and wherein said NK cells of step (a) comprise at least 40-90% CD56+/CD3− cells.

7. The method of claim 1, wherein said washed and concentrated first and second portions of said expanded NK cell fraction generated by step (d) are characterized by the following parameters:

(a) at least 70% CD56+/CD3− cells;

(b) at least 70% viability;

(c) fewer than $5.0 \lambda 10^5$ CD3+ cells/Kg mass of patient, upon infusion;

(d) no more than 5 EU endotoxin/Kg mass of patient, upon infusion; and (e) no Gram-positive micro-organisms.

* * * * *